United States Patent [19]

Weigel

[11] Patent Number: 4,584,402

[45] Date of Patent: Apr. 22, 1986

[54] DIHYDROXYACRYL

[75] Inventor: Paul H. Weigel, Dickinson, Tex.

[73] Assignee: Board of Regents, The University of Texas System, Austin, Tex.

[21] Appl. No.: 665,804

[22] Filed: Oct. 29, 1984

[51] Int. Cl.⁴ .............................................. C07C 149/23
[52] U.S. Cl. ................................................... 564/154
[58] Field of Search ......................................... 564/154

[56] References Cited

U.S. PATENT DOCUMENTS 3,883,299  5/1975  Baumgarte et al. ................. 8/34
4,154,747  5/1979  Epple et al. ....................... 260/380
4,180,308 12/1979  Mancini et al. ................ 351/160 H
4,390,683  6/1983  Yatsu et al. ....................... 528/194
4,401,372  8/1983  Mancini et al. ................ 351/160 H

OTHER PUBLICATIONS

Raja et al., J. Cell. Biol., vol. 97, p. 314a, Nov. 1983.
Weigel et al., Meth. in Enzymol., vol. 83, pp. 294–299, 1982.
Shainoff, Biochem. Biophys. Res. Comm., vol. 95, No. 2, pp. 690–695, 1980.
Fiddler et al., Anal. Biochem., vol. 86, pp. 716–724, 1978.
Mosbach et al., Meth. in Enzymol., pp. 53–65, 1976.
Ternynck et al., FEBS Lett., vol. 23, No. 1, pp. 24–28, 1972.
Weston et al., Biochem Biophys. Res. Comm., vol. 45, No. 6, pp. 1574–1580, 1971.

Primary Examiner—Paul R. Michl
Assistant Examiner—Alex H. Walker
Attorney, Agent, or Firm—Arnold, White & Durkee

[57] ABSTRACT

A compound of the formula:

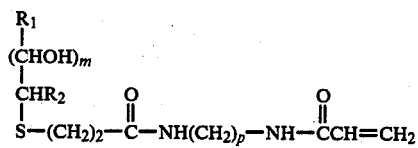

where p is a whole integer from 1 to 12, and where $R_1$ is $CH_2OH$ or $CH_2SH$ or $CHO$, m is a whole integer from 1 to 3 and $R_2$ is H or $CH_2OH$. When incorporated into acrylyl-type terpolymers, the above compounds become pendant vicinal dihydroxyalkyl substituents oxidizable by metaperiodate to a pendant aldehyde form. Molecules, including proteins, bearing at least one primary amino group are coupled to the pendant aldehyde groups through Shiff base linkages followed by alkali metal cyanoborohydride reduction of the Schiff base linkages to secondary amine linkages. The study of cell adhesion to and interactions with specific molecule-bearing synthetic cell culture surfaces as well as production of specific molecule-bearing chromatographic media and enzymic reactors are enhanced or made available through the use of the invention's vicinal dihydroxyalkyl bearing acrylyl-type terpolymers.

5 Claims, No Drawings

DIHYDROXYACRYL

The development of the present invention was supported in part by a grant from the U.S. Department of Health Education and Welfare.

BACKGROUND OF THE INVENTION

In manifold aspects of modern technology, particularly biotechnology, a need is present for methods of covalently binding molecules to solid matrices. While numerous methods of accomplishing these covalent bindings have been used or proposed, none have proven to be without technical difficulties and to be applicable in all situations. A most common method heretofore utilized for the binding of protein molecules to a solid matrix, for example, has been the reaction of proteins with polysaccharides such as Sepharose activated by cyanogen bromide [Axen et al. Nature (1967) 214 1302–1304]. This cyanogen bromide mediated binding however appears to produce an unstable covalent linkage [Tessen et al. (1973) FEBS Lett 23 56–58]. This procedure also introduces undesired positive charge into the matrix. The utilization of polyacrylamide matrices activated with glutaraldehyde to provide an aldehyde binding site for primary amino groups of proteins has been proposed [Weston et al. (1971) Biochem Biophys. Res. Comm. 45 1574–1580 and Ternynck et al. (1972) FEBS Lett 23 24–28] although later demonstrated not to be quantitatively dependable. Fiddler et al. [Anal. Biochem (1978) 86 716–724] demonstrated a method of derivatizing an aminoalkyl polyacrylamide gel (Aminoethyl Bio-Gel P-150) by treatment of the gel with glyceraldehyde followed by borohydride reduction of the resultant Schiff base to form a 1,2 dihydroxyalkyl Bio-Gel derivative. The dihydroxyalkyl Bio-Gel was then oxidized with aqueous metaperiodate to form an alkyl aldehyde Bio-Gel which was reacted with proteins bearing primary amino groups to form Schiff base linkages therewith. The Schiff base linkages were then reduced to stable secondary amine linkages by reduction with sodium cyanoborohydride.

Aminoethyl Bio-Gel P-150 is prepared by derivatizing polyacrylamide beads and is generally acknowledged by those skilled in the art to be positively charged due to the amine group substitutes. This positive charge lends itself to undesired antigenicity and may also permit non-specific ionic binding of charged molecules to the matrix. The chemical composition of the derivatized aminoethyl Bio-Gel P-150 matrix is incompletely defined. The Fiddler et al. reference is preferably limited to the use of pre-formed polyacrylamide beads with available amino groups; it is unusable for the de novo synthesis of various derivatized polyacrylamide physical forms.

Shainhoff [Biochem. Biophys. Res. Comm. (1980) 95 690–695] describes an acetaldehydic agarose derivative prepared by the coupling of glycidol and agarose followed by periodate oxidation of the alkyl 1,2-dihydroxy agarose to an aldehydic form. Binding of primary amine-bearing proteins to the aldehydic agarose was facilitated by sodium cyanoborohydride reduction of Schiff base linkages formed therebetween.

Agarose is acknowledged to be susceptible to attack by certain polysaccharide-hydrolyzing enzymes and is also potentially modifiable by treatment with inorganic periodates and moderately elevated pH levels. Agarose, being a polysaccharide, has significant antigenic potential and is also susceptible to undefined modifications by treatment with strong alkali such as 1M NaOH in the presence of NaBH$_4$. The limited physical strength of agarose represents a limit on the potential physical uses of agarose derivatives.

In U.S. Pat. Nos. 4,180,308 and 4,401,372, both issued to Mancini et al., hydrogel contact lenses of hydrated terpolymers comprising dihydroxylalkylacrylate or methacrylate were disclosed. These monomers contain a potentially unstable ester group between the dihydroxy group and the matrix. U.S. Pat. No. 3,883,299, issued to Baumgarte et al. disclosed a textile dyeing process with sulfur dyes and reductones such as 2,3-dihydroxyacrylaldehyde. U.S. Pat. No. 4,154,747, issued to Epple et al., disclosed a process for producing 1-amino-8-nitro-4,5-dihydroxyanthroquinone, one step of which entailed the reductive use of 2,3-dihydroxyacryaldehyde. U.S. Pat. No. 4,390,683, issued to Yatsu et al., disclosed a stretched poly-1,3-phenylene terephthalate film optionally comprising 3-hydroxyphenyl 1,2-dihydroxyacrylate.

All of the procedures described above have one or more of the following potential disadvantages. (a) The linkage between the dihydroxy functional group and the matrix is chemically unstable, which can result in leakage or loss of ligand. (b) High levels of ionic charge are present in the matrix which can promote non-specific and unwanted interactions with other molecules and which can make the matrix antigenic. (c) The chemical composition and nature of all functional groups in derivatized matrices are unknown. This may preclude efficient chemical utilization of the matrix, may increase the non-specific binding of undesired molecules to these unknown side products and may prevent approval of the matrix for use in humans.

SUMMARY OF THE INVENTION

A compound of the formula:

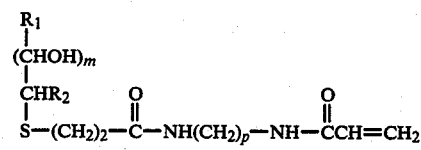

where R$_1$ is CH$_2$OH, CHO or CH$_2$SH, m is a whole integer from 1 to 3, R$_2$ is H or CH$_2$OH and p is a whole integer from 1 to 12. A terpolymer prepared from the polymerization of a mixture comprising acrylyl units, crosslinking agent and an above-described compound.

DESCRIPTION OF THE PREFERRED EMBODIMENTS

The present invention comprises a new dihydroxyacrylyl family of compounds, polyacrylyterpolymers incorporating said new compounds, and methods of using these terpolymers to covalently attach molecules bearing at least one primary amino group. The new terpolymer matrices produceable by the practice of the present invention have numerous advantages over matrices presently available. Said new terpolymer matrices may, for example, be tailored to be nonantigenic and resistant to physiological degradation, to have amino-bearing molecules stably attached thereto, to be produced in any desired physical form, to be activated at will for coupling to amino-bearing molecules, and to be completely defined in the chemical and physical sense.

Acrylyl monomers bound through a sulfur ether linkage to vicinal dihydroxy alkyl pendant functions represent a new family of compounds useful in the practices described in the present invention. Said vicinal dihydroxy alkyl acrylyl monomers are includable in acrylterpolymer synthetic schemes to produce terpolymers having pendant vicinal alkyl dihydroxy functions susceptible to periodate oxidation to form pendant alkyl aldehydes. These aldehyde terpolymers may, in turn, be coupled to molecules bearing at least one primary amino group by methods discussed later herein. The acrylyl monomers of the present invention have the vicinal alkyl dihydroxy functions connected through molecular bridges resistant to breakdown under physiological or routine laboratory conditions. Ester and disulfide bonds connecting the acrylyl function to the vicinal dihydroxy alkyl function are preferably avoided, as these linkages are susceptible to acid or base hydrolysis and rupture by thiols.

EXAMPLE 1

Synthesis of N-[methyleneaminocarbonyl 2-(1-thioyglycerol)ethyl] acrylamide, the monoaddition product between thioglycerol and bisacrylamide N,N'-methylene bisacrylamide (7.71 g or 50 mmol in 100 ml 50% ethanol) was mixed with 10 ml of pyridine (as a catalyst) in a round bottom flask. 1-Thioglycerol (2.7 g or 23.5 mmol) was dissolved in 20 ml of 50 ethanol and added dropwise through an addition funnel over 15 min in order to prevent a local excess of thioglycerol relative to bisacrylamide and to minimize the amount of di-addition product formed. After 40 min the reaction mix was rotary evaporated; heating the reaction mix to no higher than 35°–40° C. The solids left behind were dissolved in 50 ml distilled water, and extracted 5 times with 150 ml of ethyl acetate saturated with water. The aqueous layers were pooled and evaporated or lyophilized to obtain the thioglyceryl bisacrylamide adduct. Aliquots of the aqueous layer were analyzed by thin layer chromotography or silica gel using a solvent system of ethyl acetate: acetic acid: water (3:2:1, v/v). The respective $R_f$'s of the bisacrylamide, mono-adduct and di-adduct are 0.93, 0.79 and 0.55 in this solvent system. The bisacrylamide and monoadduct were visualized by ultraviolet light. All products, including the di-adduct, were visualized with a permanganate/periodate spray for reducing compounds. ($KMnO_4$, 2 mg/ml; $Na_2CO_3$, 4 mg/ml; $NaIO_4$, 16 mg/ml).

Silicic acid partition column chromatography was done to achieve the final purification. The silica gel was oven dried for 1 hour at 110° C. to activate the silica prior to packing the column. For 5 gm of the lyophilized extracted reaction mix, a 550 ml column (2.7 cm×95 cm) of silica gel was packed in ethyl acetate: acetic acid: water (3:2:0.5, v/v). The column was washed with 5 column volumes of solvent prior to loading the sample, which was dissolved in 50 ml of the same solvent. Fractions of 7.5 ml were collected and analysed by thin layer chromatography (TLC) with the 3:2:1 solvent system and by a permaganate spectrophotometric assay. As seen by both TLC and the spectrophotometric assay, chromatographic separation of all components was achieved, the order of elution being the unreacted N,N' methlenebisacrylamide followed by the mono-adduct of thioglycerol to the bisacrylamide and finally the di-adduct. Those fractions containing the mono-adduct were pooled, rotary evaporated, dissolved in 50% ethanol, rotary evaporated again, dissolved in $H_2O$, lyophilized, weighed and stored. The final yield of the monoaddition product was 3.4 gm (55%). The solvent extraction step can be omitted and the lyophilized or evaporated reaction mix can be chromatographed directly as described above.

The product was pure as judged by TLC and contained both acryloyl and vicinal alkyl hydroxyl groups. Elemental analysis, performed by Galbraith Laboratories (Knoxville, Tenn.) gave the following results consistent with the formula: $C_{10}H_{18}O_4N_2S$ (MW=262.33). Theoretical values are in parentheses: 46.13 (45.79) % C; 6.65 (6.92) % H; 10.63 (10.68) % N; 12.67 (12.22) % S. The product has the following structure:

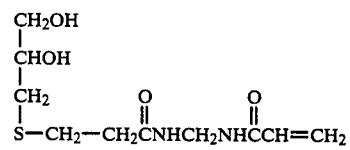

which is also shown by the formula:

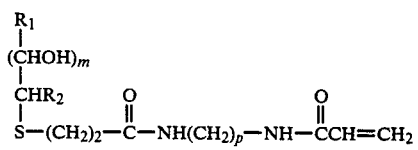

where $R_1$ is $CH_2OH$, m is 1, $R_2$ is H and p is 1.

By analogous procedures similar adducts of other vicinal dihydroxy alkyl thiols may be produced. For example, dithiothreitol, dithioerythritol, 5-thio D-glucose or 5-thio D-glucitol, all commonly available, may be substituted for the thioglycerol to obtain analogous acryl compounds having vicinal dihydroxy alkyl substituents bound through a sulfur-ether linkage. In addition to substitutes for the thioglycerol reactant in the production of compounds of the present invention, substitutes may be made for the N,N' methylenebisacrylamide. These latter substitutes include commerically available N,N' ethylenebisacrylamide, N,N' trimethylenebisacrylamide, N,N' tetramethylenebisacrylamide, N,N' hexamethylenebisacrylamide and N,N' dodecanomethylenebisacrylamide. Other N,N' (methylene)bisacrylamides having methylene bridges numbering from 5 to 12, may be made by well established procedures.

Utilizing various combinations of the above-described alternatives, compounds having the following formula may be readily synthesized:

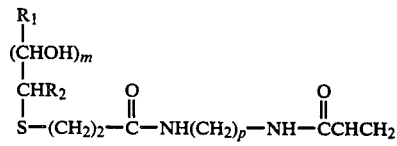

where p is a whole integer from 1 to 12 (depending on the particular N,N' p-methylenebisacrylamide used) where p is a whole integer from 1 to 12. When 1-thioglycerol is used, m is 1, $R_1$ is $CH_2OH$ and $R_2$ is H. If dithiothreitol is used in place of 1-thioglycerol, $R_1$ is $CH_2SH$, m is 2 and $R_2$ is H. If 5-thio-D-glucose is used in place of 1-thioglycerol, $R_1$ is CHO, m is 3 and $R_2$ is CH$_2$OH. If 5-thio-D-glucitol is used in place of 1-thioglycerol R$_1$ is CH$_2$OH, m is 3 and R$_2$ is CH$_2$OH.

Further compounds having an acrylyl function and an amide-bound vicinal dihydroxyalkyl portion may be produced by commonly utilized synthetic procedures. For example, acryloyl chloride or methacryloyl chloride may be coupled, under substantially anhydrous conditions to primary amines bearing vicinal dihydroxyalkyl substituents such as 1-amino glycerol or to reduced amino sugars such as glucosaminitol or galactosaminitol. Amides rather than esters are preferentially formed because the reactivity of amines for such reactions is well known to be much greater than the reactivity of hydroxy groups under similar conditions. Undesired esters, present as minor side products, can be easily removed by mild alkalai treatment [Weigel et al. *Methods in Enzymology*, Vol. 83 (1982) pp. 294–299]. As a result of such couplings between the acyl chloride and compounds of the formula:

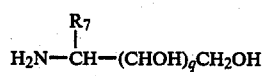

where q is a whole integer between 1 and 3 and R$_2$ is H or CH$_2$OH, vicinal dihydroxy alkyl acrylamides will be formed of the formula:

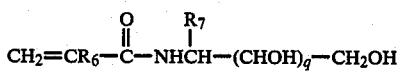

where R$_6$ is H or CH$_3$, R$_7$ is H or CH$_2$OH and q is a whole integer between 1 and 3.

Various other synthetic schemes using reagents and conditions established in the art may be utilized to produce acrylyl-type derivatives containing vicinal dihydroxyalkyl functions by the use of new dihydroxalkyl reactants. For example, acryloyl or methacryoyl chloride may be reacted with an aminocarboxylic acid such as 5-aminocaproic acid to produce a first compound having the formula:

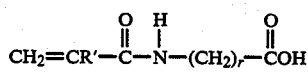

where R' is H or CH$_3$ and r is 5. This first compound is then reacted with N-hydroxysuccinimide and dicylohexylcarbodiimide to form an N-succinimidl derivative of the formula:

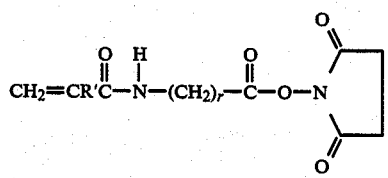

The N-succinimidl derivative will react with a vicinal dihydroxyalkyl amine such as 1-aminoglycerol, for example, to produce a second compound of the formula:

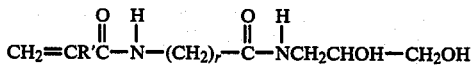

which could be utilized as a component in an acrylyl-type terpolymer to add desired amounts of pendant vicinal dihydroxyalkyl substituents thereto.

A further synthetic scheme to produce such an acrylyl compound bearing a vicinal dihydroxyalkyl substituent may comprise first reacting a halogenated alkyl carboxylic acid such as 3-bromopropionic acid, for example, with a vicinal dihydroxyalkyl thiol or amine, 3-mercaptoglycerol, for example, to produce a vicinal dihydroxyalkylcarboxyl-containing compound of the formula:

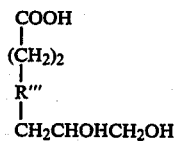

where s is 2 and R''' is S or NH. Acryloyl or methacryoyl chloride may be reacted with a diamine, such as 1,6 diaminohexane for example, to produce an aminoacrylyl compound of the formula:

where R' is H or CH$_3$ and t is 6. The vicinal dihydroxyalkylcarboxyl-containing compound may then be reacted with the aminoacrylyl compound, in the presence of dicyclohexylcarbodiimide to form a product compound of the formula:

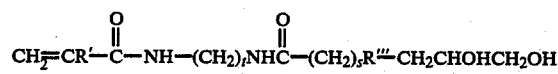

where R' is H or CH$_3$, t is 6, s is 2 and R''' is S or NH. This product compound may be included in an acrylyl-type co-polymer to provide a polymer comprising pendant vicinal dihydroxyalkyl substituents.

The aminoacrylyl compound discussed above of the formula

may alternatively be reacted in the presence of an alkali metal cyanoborohydride or alkali metal borohydride with a vicinal dihydroxyalkylaldehyde such as glyceraldehyde, for example. Such a reaction will produce a vicinal dihydroxyalkylacrylyl compound of the formula:

Yet another synthetic scheme utilizing synthetic steps well known in the art first involves the reaction of N,N' methylenebisacrylamide with hydrobromic acid to produce the monobromo adduct of the formula:

When this monobromo adduct is reacted with an amino or thiol vicinal dihydroxy alkyl compound, such as thio or amino glycerol for example, a vicinal dihydroxyalkyl-acrylyl adduct will be formed of the formula:

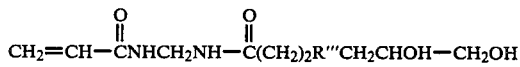

where R''' is S or NH. This represents a different route to the newly synthesized compound of the present invention, the only difference being the alternative inclusion of NH or R'''.

Given the schemes and reagents available in modern sythetic chemistry, the above-described methods of synthesis are but examples to indicate various reagents, linking chains and reactions usable to produce vicinal dihydroxyalkyl acrylyl compounds which may be utilized to produce terpolymers bearing pendant vicinal dihydroxyalkyl substituents activatable by metaperiodate to aldehydic forms useful for the binding of molecules bearing at least one primary amino group.

Further methods of synthesizing such vicinal dihydroxyalkyl-acrylyl adducts, once knowledge of the advantages and usefulness thereof as delineated in the present specification are known, are available in well documented synthetic schemes.

EXAMPLE 2

Synthesis of terpolymer comprising acrylamide, N,N¹-methylenebisacrylamide and N-[methyleneaminocarbonyl 2-(thioglycerol)ethyl] acrylamide Flat polyacrylamide gels or terpolymers (copolymers) with varying amounts of pendant vicinal dihydroxyalkyl functions were sythesized as synthetic surfaces useful for studies of eucaryotic cell adhesion. A stock solution containing 60% (w/v) acrylamide and 3% (w/v) N,N'-methylenebisacrylamide [Weigel et al. Methods in Enzymology, Vol. 83 (1982) pp. 294–299] was used in combination with other substances as indicated below to form an aqueous polymerization mixture. The polymerization mixture, in a volume of 1.43 ml, contained: 50 mM sodium phosphate (or phosphate-buffered saline); 20% (w/v) acrylamide; 1% (w/v) N,N'-methylenebisacrylamide; 0.17% (v/v) N,N,N',N'-tetramethyleneethylenediamine; 0.2% (w/v) ammonium persulfate and N-[methyleneaminocarbonyl 2-(thioglycerol)ethyl] acrylamide, also at concentrations ranging from about 10 mM to about 242 mM. Polymerization was initiated by ammonium persulfate addition and allowed to proceed at room temperature for about 60 min. The gel was polymerized between acid cleaned glass plates separated by a thin silicone rubber gasket. These polymerization conditions give at least a 90% conversion of monomers into the polymer [Weigel et al., ibid]. The gel pieces were washed six times with phosphate buffered saline and no unreacted monomers were detected after the third wash.

The gel pieces were oxidized with 20 mM NaIO$_4$, in 20 mM sodium phosphate, pH 6.6, for 60 min at 0° C. to convert pendant vicinal dihydroxyalkyl functions free formaldehyde and to pendant alkyl aldehydes on the matrix. The formaldehyde in the supernatant solutions was measured by the chromotropic acid assay described by E. D. Korn [Methods in Biochemical Analyses (1959) Vol. 7, p. 179]. When calculated on the basis of nmols formaldehyde released/cm$^3$ gel matrix volume, it was found that a linear relationship existed between aldehyde content in the matrix and the concentration of N-[methyleneaminocarbonyl 2-(thioglycerol)ethyl] acrylamide in the polymerization mixture, i.e., 242 mM N-[methyleneaminocarbonyl 2-(thioglycerol)ethyl] acrylamide gave a gel having about 189 micromols aldehyde per cm$^3$ of gel; 121 mM, 101 micromols/cm$^3$; 40 mM, 30 micromols/cm$^3$; 20 mM, 19 micromols/cm$^3$ and 10 mM, 8.5 micromols/cm$^3$.

Although acrylamide in major amount was utilized to synthesize the above-described embodiment of the present invention, numerous acrylamide derivatives are commercially available and usable to substitute for part or all of the acrylamide to synthesize vicinal dihydroxyalkylacryl terpolymers having a variety of physical properties. These monomers are represented by the formula:

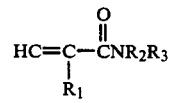

where $R_1$ is H or $CH_3$, $R_2$ is H and $R_3$ is benzyl, methbenzyl, n-butyl, t-butyl, p-chlorophenyl, cyclohexyl, dodecyl, ethyl, methyl, n-hexadecyl, 1-napthyl, p-nitrophenyl, n-octadecyl or 2-phenethyl. In several cases where $R_1$ is H or $CH_3$, $R_2$ and $R_3$ are the same and are n-butyl, ethyl or methyl.

Other cross-linking agents may be used in combination with or in place of N,N'-methylenebisacrylamide to form polymers with various physical characteristics such as altered porosity, strength or susceptibility to chemical cleavage. These commercially available cross-linking agents include bis-acryloyl cystamine, N,N' hexamethylenebisacrylamide, N,N'(bisethylsulfone)-bisacrylamide, N,N' diallyltartardiamide, N,N'-(1,2 dihydroxyethylene) bisacrylamide, N,N' ethylenebisacrylamide, N,N' dodecanomethylenebisacrylamide, and N,N' trimethylenebisacrylamide.

Acryloyl terpolymers such as those described above may also be synthesized in bead forms suitable for uses such as column chromatography media, for example. The bead-polymerization process employs polymerization in an aqueous polymerization mixture as described above, but while said aqueous mixture is suspended as liquid granules in an immiscible solvent phase [Mosbach et al., Methods in Enzymology, Vol. 44 (1976) pp. 53–68].

When the terpolymer is prepared in aqueous solutions as described herein, a major amount of acrylamide or other substituted acrylyl unit is preferably between about 5% (w/v or weight/volume) and about 30% (w/v), most preferably, as for the preparation of cell culture surfaces as described herein for example, about 20% (w/v); a minor amount of crosslinking agent is preferably between about 0.1% (w/w) and about 5% (w/w), based on the weight of acrylamide, most preferably about 1% (w/w); and a lesser amount of an acrylyl compound can range from about 10 mM up to about 500 mM or even greater if desired. If necessary the acrylyl monomer may even substitute for acrylamide to give essentially a homopolymer.

A terpolymer bearing pendant vicinal dihydroxyalkyl substituents in bead form or a form having a flat surface may also be synthesized by the procedures described herein but using the vicinal dihydroxyalkyl acrylamides of the formula:

$$CH_2=CR_6CNHCH(CHOH)_qCH_2OH$$
with $\overset{O}{\underset{\|}{C}}$ and $R_7$ substituent shown where $R_6$ is H or $CH_3$, $R_7$ is H or $CH_2OH$, and q is a whole integer from 1 to 3. The procedure as described in Example 2 will be modified only in that the N-[methyleneaminocarbonyl 2-(thioglycerol)ethyl] acrylamide would be replaced by equivalent concentrations of the above compound. The resultant terpolymer will be oxidizable by metaperiodate to an aldehyde form and analogously coupled to molecules bearing primary amines.

EXAMPLE 3

Coupling of hyaluronic-amine, Ethanolamine or protein to an aldehydic polyacrylyl matrix In the following study, the ability of a variety of biomolecules of widely differing size to be covalently attached to the newly developed aldehydic polyacrylyl matrix was demonstrated. The rate and extent of coupling and its dependence on the concentration of the soluble biomolecule and the dihydroxy acrylyl group in the matrix were determined.

Hyaluronic acid oligosaccharides of various molecular weight ranges (as desired) were obtained by partial enzymatic digestion of purified hyaluronic acid from human umbilical cord (Sigma Chemical Co.) followed by gel filtration chromatography. The oligosaccharides thus obtained were reduced with sodium borohydride (Matheson, Coleman and Bell) and then partially oxidized with $NaIO_4$ to form hyaluronate aldehyde. The hyaluronate aldehyde (7.750 umol) was mixed well with hexanediamine (11.63 umol) in 1.15 ml water and added to a vial containing 10 mCi of $^3H$-$NaCNBH_3$ according to the general procedure of Raja et al. [Anal. Biochem. (1984) Vol. 34, pp. 168-177]. The reaction mix was stirred at room temperature for 14 hr and $^3H$-hyaluronate-amine was recovered from the reaction mix by ethanol precipitation. The precipitate of $^3H$-hyaluronate-amine was suspended in phosphate buffered saline (PBS) and fractionated over a Bio-Gel P2 column in PBS. Aliquots of the column eluates were assayed for $^3H$-radioactivity. Fractions in the first peak of radioactivity (eluting in the column void volume) were pooled and assayed for total sugar and amino groups. The specific radioactivity obtained was 5759 cpm per nmol of amine.

Twenty-five microliters of a 0.5 mg/ml solution of 1,3,4,5-tetrachloro-3a,6a glycouril (iodogen) from Pierce Chemical Co. in dichloromethane was evaporated from the bottom of a 12×75 mm glass tube. Bovine serum albumin (BSA; 500 ug in 250 ul PBS) was placed in the tube on ice and them mixed with 1 mCi of $^{125}I$-NaI (5 mCi/mg, Amersham Corp.). The solution was kept on ice for 30 min with occasional swirling and then loaded on a 5 ml Sephadex G-25 column. This column had been pretreated with BSA (to eliminate non-specific binding) and subsequently washed with PBS. The void volume fractions were pooled and stored at 0° C. The specific radioactivity of $^{125}I$-BSA was 2.76×10$^7$ cpm per ug.

Square polyacrylamide gel pieces (8mm×8mm×0.25mm) containing the appropriate concentration up to 189 mM dihydroxy alkyl acrylyl monomer were oxidized with 10 mM $NaIO_4$, pH 6.6 at 0° C. for 30 min. The oxidized gels containing up to 189 mM aldehyde were washed twice with 0.05M sodium borate (pH 8.0), blotted to remove excess liquid, and transferred to tissue culture wells (2 ml) containing the desired concentration of an amine compound in 50 mM sodium borate, pH 8.0. Only one gel piece was present per well. The gels were agitated gently on a platform shaker at 150 rpm for 5-10 min at room temperature and 96 ul of 2M $NaCNBH_3$ in sodium borate was added to each well. Agitation was continued for up to 20 hr for reactions with up to 300 mM $^{14}C$-ethanolamine and up to 48 hrs with up to 23 mg/ml $^{125}I$-BSA and 10 mM $^3H$-hyaluronate. At the end of the reaction periods the gels were transferred to fresh wells containing 1.0 ml of 1M $NaBH_4$ and agitated for 5 hrs. This treatment reduces any unreacted aldehyde groups in the matrix to hydroxyl groups. The reduced gels were washed 4 times with PBS. In cases where the amino molecule was radiolabelled with $^3H$ or $^{14}C$, the gel pieces were blotted briefly, and transferred to glass vials containing 600 ul of 30% $H_2O_2$. These vials were sealed and heated at 55° C. for 15 hr to solubilize the polyacrylamide matrix. Five hundred ul aliquots of the solubilized gels were mixed with 4.5 ml scintillation fluid and $^{14}C$- or $^3H$-radioactivity was determined. The amount of radioiodinated amine coupled to the matrix was determined directly by a Beckman gamma 4000 Spectrometer.

The results of this study showed that $^{14}C$-ethanolamine covalently bound to the polyacrylamide matrix reached a near maximal level of about $1\times10^4$ pmol per cm$^2$ gel surface within about 1 hr. The binding of $^3H$-hyaluronate amine analogously was about $1\times10^3$ pmol per cm$^2$ within about 4 hr. The binding of $^{125}I$-BSA analogously was about 0.25 pmol per cm$^2$ after about 20 hr. The smaller amine-bearing molecules react more swiftly and to a greater extent, presumably because of their greater access to aldehydic groups within the gel matrix. The extent of coupling of amino-bearing molecules to aldehydic polyacrylamide matrix was found to be directly related to the concentration of the amino-molecule and to the gel aldehyde content and inversely related to the size of the amine-bearing molecules.

Since the amount of immobilized BSA was very low, in the pmol range, it was necessary to demonstrate that this BSA was in fact covalently linked to the matrix and was not just electrostatically associated or nonspecifically adsorbed to it. To test this, gels containing the bound protein were treated with either 1% sodium dodecyl sulfate (SDS) at 55° C. for 20 min or with 5M NaCl at 22° C. for 15 min and the $^{125}I$-radioactivity released into the supernatant solution was determined. The $^{125}I$-radioactivity released in the presence of 1% SDS was less than 10% and that released into the 5 m NaCl supernatant was less than 2% of the total $^{125}I$-radioactivity associated with the matrix. This confirms that the large majority of $^{125}I$-BSA associated with the gel was in fact covalently linked to the activated polyacrylamide matrix.

As the above examples demonstrate, polyacrylamide gel matrices containing any type of covalently bound molecule bearing at least one primary amino group may be prepared by practice of the present invention.

The advantages and potential uses of the products produceable by use of the compounds and procedure of the present invention are extensive and apparent to those skilled in the art upon examination of this specification. An application most extensively described herein discloses the use of the present invention to prepare gel surfaces suitable for studies relating to eucaryotic or procaryotic cell adhesion and cell culture.

Generally, a new process for covalently binding molecules bearing at least one primary amino group to a polyacrylyl terpolymer is contained herein. This process comprises first providing a quantity of polyacrylyl terpolymer bearing pendant vicinal dihydroxyalkyl substituents bound to said terpolymer through carbon-carbon and carbon-sulfur or carbon-nitrogen linkages. Said linkages provide resistance to rupture under commonly desired conditions of temperature, pH and presence of thiols.

The polyacrylyl terpolymer is oxidized with an alkali metal metaperiodate such as sodium metaperiodate, for example, although metaperiodic acid could also be utilized. The oxidized terpolymer has pendant alkyl aldehyde substituents having been formed from at least a portion of the vicinal dihydroxyalkyl substituents. The oxidized terpolymer, preferably after washing away excess periodate and unbound oxidation products, is incubated with molecules bearing at least one primary amino group to form Schiff base linkages between the amino groups and the pendant aldehyde substituents. This incubation is preferably done in the presence of an alkali metal cyanoborohydride such as sodium cyanoborohydride, which selectively reduces Schiff base linkages to secondary amines, although the reduction may be carried out as a following step.

The molecules bearing at least one primary amino group are, in many cases, proteins such as enzymes or antibodies, although any compound such as a drug or metabolite, for example, bearing a primary amino group may be similarly coupled to the acrylyl-type terpolymer described herein. A final preferable step is to react the acrylyl-type terpolymer bound to the molecules through secondary amine linkages with alkali metal borohydride, most preferably sodium borohydride, to reduce any residual unreacted pendant aldehyde substituents to alkyl alcohol substituents. This final step lessens the opportunities for future non-specific binding to the product terpolymer.

Although cells can recognize and adhere to each other by interactions between molecules that are present on the cell surface, the molecular events underlying these processes are not fully understood. A major difficulty in studies on the biochemical basis of cellular interactions is the complexity of the extracellular matrix. The synthetic culture surfaces described herein can facilitate controlled studies on cellular interactions with a particular biomolecule without interference from unknown factors that are present in a complex extracellular matrix. Polyacrylamide matrices have a number of advantages for use as the physical support in such biochemical investigations: (1) Polyacrylamide is non-toxic, optically transparent and chemically inert. (2) The shape, size and porosity of the matrix can be varied as desired; gels can be made as flat surfaces suitable for cell culture or as beads for use in column chromatography. (3) There are no enzymes known that degrade or modify polyacrylamide. (4) The concentration of cell-binding ligand in the matrix can be varied as desired without affecting other parameters. (5) The carbon-nitrogen and carbon-sulfur bonds linking the ligand to the matrix are more stable than most other bonds used for such linkage purposes. (6) A large number of acryloyl monomers are commercially available or can be readily synthesized and used in combination with the dihydroxyacryl compound of the present invention to produce gels with the desired physical characteristics. These gels are able, after periodate activation, to couple any chosen molecule bearing at least one primary amino group.

Polyacrylamide matrices have been synthesized according to the present invention that contain known amounts of particular types of molecules. The synthetic scheme described herein is a general one which can be used to link covalently any amino-containing molecule to the aldehyde-activated polyacrylamide matrix. For example, proteins, glycoproteins, glycopeptides, small amines or synthetic amine derivatives of glycolipids, complex glycosaminoglycans or simple sugars can be immobilized by this method. The reactions described here can also be used to link two or more different molecules (for example, a protein and a carbohydrate derivative), to the same surface. Such complex matrices can be used to assess the influence of one component on the ability of cells to interact with another component. The complexity of such matrices can be increased stepwise so that they more closely simulate an in vivo situation. It is also possible to prepare cell culture surfaces with a continuous or discontinuous gradient of the ligand by first synthesizing the polyacrylamide matrix with a gradient [Margolis et al. (1968) Anal. Biochem., Vol. 25, pp. 347–362] of the thioglyceryl bisacrylamide mono-adduct or analogous adduct and then coupling the desired amine compound to the oxidized gels. It is also possible to generate three dimensional polyacrylamide-based cell binding matrices, using the related hydroxy methacrylate derivative, with sufficiently large pores to accommodate cells [Kristonpil et al. (1973) J. Chromat., Vol. 76, pp. 274–276].

The amount of amine coupled to the gel can be manipulated by varying the concentration of amino groups in the reaction mixture or by varying the aldehyde content of the polyacrylamide matrix. It is important to be able to control and to vary the amount of biomolecule that is immobilized on a synthetic culture surface because cells may require a critical concentration of the particular protein or sugar, etc., in order to bind to, spread on or grow on the surface. If the concentration of the biomolecule on a culture surface is below that required for a threshold binding response, then a false negative result may be observed. Culture surfaces, prepared by the physical adsorption of proteins or glycolipids onto plastic or glass surfaces have many disadvantages compared to the system described here. In the case of proteins, the process of adsorption can lead to denaturation and loss of activity and/or native structure. Since the attachment is not covalent, it can also be reversed. Displacement by other molecules can occur and the composition of the surface can change during the experiment. Furthermore, since most serum or cell secreted proteins adsorb well to glass or plastic, these substrata elicit a positive response (i.e. binding) from cells. The system presented here has been specifically developed so that cells do not interact with or bind to the background matrix itself.

Another advantage of the synthetic scheme described here is that the amino molecule is linked to the polyacrylamide matrix (PAM) by a long spacer arm, for example:

(PAM—CH$_2$—CH$_2$—CO—NH—CH$_2$—NH—CO—CH$_2$—CH$_2$—S—CH$_2$—CH$_2$—NH—R), where R is the bound molecule. This makes it more likely that the bound amino molecule is freely accessible to interact with cells or other soluble proteins despite being immobilized. In the case of cell culture surfaces prepared by adsorption of molecules into plastic surfaces, portions of the adsorbed molecule may be "cryptic" because they interact with a large area of the plastic surface.

General uses for these or similar polyacrylamide matrices containing immobilized biomolecules prepared as described here include the following:

(1) Direct isolation and characterization of cell surface receptors or binding proteins for the molecule immobilized on the polyacrylamide culture surface;

(2) Aldehyde-activated polyacrylamide matrices (in the form of beads) provide a mild way to covalently link enzymes and therefore are applicable to the design of enzyme reactors;

(3) Polyacrylamide matrices containing appropriate radioactive substrate proteins can be used as solid phase reagents for detecting and quantitating protease activity;

(4) Since these matrices are non-charged, chemically well defined and non-antigenic they could be used as a vehicle (carrier) for the delivery of drugs or antibodies in vivo. They may be useful in clinical applications.

(5) Immobilization of antigens, such as proteins, on these matrices may improve the efficiency of raising monoclonal antibodies to soluble or low molecular weight molecules. It is generally recognized that antibody production to soluble molecules occurs poorly. Therefore attachment to a large insoluble, non-antigenic carrier could be very useful.

Major advantages of a matrix prepared according to the present invention over other existing matrix preparing procedures include:

(1) The matrix is chemically defined.

(2) The matrix is non-ionic, not antigenic and does not promote non-specific adsorption of other molecules.

(3) The covalent linkage between the matrix and amine-molecules bound to the matrix is much more stable than the bonds generally used in other procedures.

(4) The dihydroxy matrix can be prepared in advance, stored refrigerated and activated to couple an amine molecule when desired.

(5) The numerous advantages associated with polyacrylamide as enumerated above.

Changes may be made in the specific procedures, reactants, and arrangements described herein without departing from the concept and scope of the invention as described in the following claims.

What is claimed is:

1. A compound of the formula:

$$\begin{array}{c} R_1 \\ | \\ (CHOH)_m \\ | \\ CHR_2 \\ | \\ S-(CH_2)_2-\overset{O}{\underset{\|}{C}}-NH(CH_2)_p-NH-\overset{O}{\underset{\|}{C}}CH=CH_2 \end{array}$$

where p is a whole integer from 1 to 12, $R_1$ is $CH_2OH$, CHO or $CH_2SH$, m is a whole integer from 1 to 3 and $R_2$ is $CH_2OH$ or H.

2. The compound of claim 1 defined further wherein p is 1, m is 1 and $R_1$ is $CH_2OH$ and $R_2$ is H.

3. The compound of claim 1 defined further wherein p is 1, $R_1$ is $CH_2OH$, m is 1 and $R_2$ is H.

4. The compound of claim 1 defined further wherein p is 1, $R_1$ is CHO, m is 3 and $R_2$ is $CH_2OH$.

5. The compound of claim 1 defined further wherein p is 1, $R_1$ is $CH_2SH$, m is 2 and $R_2$ is H.

* * * * *

UNITED STATES PATENT AND TRADEMARK OFFICE
CERTIFICATE OF CORRECTION

PATENT NO. : 4,584,402

DATED : April 22, 1986

INVENTOR(S) : Paul H. Weigel

It is certified that error appears in the above-identified patent and that said Letters Patent is hereby corrected as shown below:

Column 3, line 28, insert --%-- between the numeral "50" and the word "ethanol".

Column 3, line 40, delete the word "chrom♀tography" and insert therefor the word --chromatography--.

Column 3, line 40, delete the word "or" and insert therefor the word --on--.

Column 4, line 64, delete "where p is a whole integer from 1 to 12".

Column 5, line 26, delete the subscript "2" located between "R" and the word "is" and insert therefor as a subscript the numeral --7--.

Column 5, line 50, delete the word "N-succinimidl" and insert therefor the word --N-succinimidyl--.

Column 5, line 61, delete the word "N-succinimidl" and insert therefor the word --N-succinimidyl--.

Column 6, line 15, delete the second occurrence of the numeral "2" and insert therefor the lowercase letter --s--.

Column 6, line 47, delete "R" and insert therefor --R'--.

Column 6, line 58, delete "R" and insert therefor --R'--.

Column 7, line 12, delete the word "or" and insert therefor the word --for--.

Column 7, line 30, delete the word "N,N$^1$-methylenebisacrylamide" and insert therefor the word --N-N'-methylenebisacrylamide--.

Column 7, line 62, insert the word --to-- between the word "functions" and the word "free".

UNITED STATES PATENT AND TRADEMARK OFFICE
CERTIFICATE OF CORRECTION

PATENT NO. : 4,584,402

DATED : April 22, 1986

INVENTOR(S) : Paul H. Weigel

It is certified that error appears in the above-identified patent and that said Letters Patent is hereby corrected as shown below:

Column 9, line 57, delete the word "them" and insert therefor the word --then--.
Column 13, line 1, insert the uppercase letter --H-- immediately after the second occurrence of the letter "N".
Column 13, line 2, delete "H--".
Column 13, line 2, insert the numeral --2-- as a subscript immediately after the last occurrence of "H".
Column 13, line 3, delete "2--".
Column 13, line 8, delete the word "into" and insert therefor the word --onto--.
Claim 3, column 14, line 36, delete the numeral "1" located between the word "is" and the word "and" and insert therefor the numeral --3--.
Claim 3, column 14, line 36, delete the letter "H" and insert therefor --$CH_2OH$--.

Signed and Sealed this

Seventeenth Day of May, 1988

Attest:

DONALD J. QUIGG

Attesting Officer

Commissioner of Patents and Trademarks